(12) United States Patent
Lebofsky et al.

(10) Patent No.: US 12,227,792 B2
(45) Date of Patent: Feb. 18, 2025

(54) MDA USING BEAD OLIGONUCLEOTIDE

(71) Applicant: Bio-Rad Laboratories, Inc., Hercules, CA (US)

(72) Inventors: Ronald Lebofsky, Kensington, CA (US); Jeremy Agresti, Richmond, CA (US); George Karlin-Neumann, Palo Alto, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 18/381,371

(22) Filed: Oct. 18, 2023

(65) Prior Publication Data

US 2024/0093268 A1    Mar. 21, 2024

Related U.S. Application Data

(60) Division of application No. 17/508,674, filed on Oct. 22, 2021, now Pat. No. 11,905,551, which is a continuation of application No. 16/012,610, filed on Jun. 19, 2018, now Pat. No. 11,186,862.

(60) Provisional application No. 62/522,226, filed on Jun. 20, 2017.

(51) Int. Cl.
| | |
|---|---|
| C12Q 1/6806 | (2018.01) |
| C12Q 1/6811 | (2018.01) |
| C12Q 1/682 | (2018.01) |
| C12Q 1/6832 | (2018.01) |
| C12Q 1/6853 | (2018.01) |
| C12Q 1/686 | (2018.01) |

(52) U.S. Cl.
CPC .......... *C12Q 1/6806* (2013.01); *C12Q 1/6811* (2013.01); *C12Q 1/682* (2013.01); *C12Q 1/6832* (2013.01); *C12Q 1/6853* (2013.01); *C12Q 1/686* (2013.01)

(58) Field of Classification Search
CPC .... C12Q 1/6806; C12Q 1/6811; C12Q 1/682; C12Q 2525/301; C12Q 2565/537
See application file for complete search history.

(56) References Cited

U.S. PATENT DOCUMENTS

| | | | |
|---|---|---|---|
| 11,186,862 | B2 | 11/2021 | Lebofsky et al. |
| 2009/0023190 | A1 | 1/2009 | Lao |
| 2013/0130919 | A1 | 5/2013 | Chen |
| 2014/0213485 | A1 | 7/2014 | Weissman et al. |
| 2014/0243242 | A1 | 8/2014 | Nicol |
| 2014/0378349 | A1 | 12/2014 | Hindson |

(Continued)

FOREIGN PATENT DOCUMENTS

| | | |
|---|---|---|
| EP | 0971039 A2 | 1/2000 |
| WO | 2012/162267 A2 | 11/2012 |
| WO | 2015/019247 A1 | 2/2015 |

(Continued)

OTHER PUBLICATIONS

International Search Report and Written Opinion from PCT/US2018/038351 mailed Sep. 27, 2018; 14 pages.

(Continued)

*Primary Examiner* — Young J Kim
(74) *Attorney, Agent, or Firm* — Kilpatrick Townsend and Stockton LLP

(57) ABSTRACT

Improved multiple displacement amplification (MDA) reagents and methods are provided.

14 Claims, 12 Drawing Sheets

Specification includes a Sequence Listing.

(56) References Cited

U.S. PATENT DOCUMENTS

2016/0060621 A1\* 3/2016 Agresti ............... C12Q 1/6806
506/4
2019/0292575 A1 9/2019 Murtaza

FOREIGN PATENT DOCUMENTS

WO 2016/126871 A2 8/2016
WO 2017/165289 A1 9/2017

OTHER PUBLICATIONS

Spits. C. et al.; "Whole-genome multiple displacement amplification from single cells"; Nature Protocols; Nature Publishing Group, GB; vol. 1, No. 4; Jan. 1, 2006; pp. 1965-1970.
Novak, et al.; "Single-Cell Multiplex Gene Detection and Sequencing with Microfluidically Generated Agarose Emulsions"; *Angewandte Chemie Int.*; vol. 50; 2011; pp. 390-395.

\* cited by examiner

MDA USING BEAD OLIGONUCLEOTIDE

CROSS-REFERENCE TO RELATED PATENT APPLICATIONS

The present application is a divisional of U.S. patent application Ser. No. 17/508,674, filed Oct. 22, 2021, which is a continuation of U.S. patent application Ser. No. 16/012,610, filed Jun. 19, 2018, which claims benefit of priority to U.S. Provisional Patent Application No. 62/522,226, filed Jun. 20, 2017, which are incorporated by reference for all purposes.

REFERENCE TO SUBMISSION OF A SEQUENCE LISTING

The instant application contains a Sequence Listing which has been submitted electronically in XML format and is hereby incorporated by reference in its entirety. Said XML copy, created on Nov. 2, 2023, is named 094868-1410318_114230US_SL.xml and is 4,856 bytes in size.

BACKGROUND OF THE INVENTION

Multiple displacement amplification (MDA) is a non-PCR based DNA amplification technique that involves use of random oligonucleotides that prime at random locations on a DNA sample. In many case, the random oligonucleotides are random hexamer primers that are annealed to the DNA. The primers are then extended with a polymerase, e.g., a strand displacing polymerase such as (D29 DNA polymerase, at a constant temperature. The resulting extension products can then be sequenced and aligned to generate a sequence of the DNA. An example of single-cell whole genome MDA is described for example in Spits et al, *Nature Protocols* 1, 1965-1970 (2006).

BRIEF SUMMARY OF THE INVENTION

In some aspects, a method of performing multiple displacement amplification is provided. In some embodiments, the method comprises, providing a plurality of oligonucleotides, each oligonucleotide comprising a 3' random sequence of at least four contiguous nucleotides, a barcode sequence, and optionally an intervening sequence, the oligonucleotides annealed to a complementary nucleic acid that is complementary to the barcode sequence, intervening sequence, or both the barcode sequence and the intervening sequence, wherein the complementary nucleic acid is not complementary to the 3' random sequence, leaving the 3' random sequence to be single-stranded;
  contacting the plurality of oligonucleotides to sample DNA under conditions in which the complementary nucleic acid anneals to an oligonucleotide and allows for annealing of the 3' random sequence to the DNA; and
  extending the 3' random sequence in a template-dependent manner with a strand-displacing polymerase to generate extended oligonucleotides comprising a 3' sequence complementary to the DNA.

In some embodiments, the plurality comprises at least 25 different oligonucleotides having different random sequences.

In some embodiments, the oligonucleotides further comprise a 5' tag sequence. In some embodiments, the tag sequence is 2-40 nucleotides long.

In some embodiments, the oligonucleotide lacks the intervening sequence and the complementary nucleic acid is complementary to the barcode sequence, or at least a 6 nucleotide contiguous portion thereof. In some embodiments, the barcode sequence is discontinuous and the intervening sequence is between two or more portions of the barcode sequence.

In some embodiments, the complementary nucleic acid does not comprise a sequence complementary to the barcode sequence.

In some embodiments, the oligonucleotides are covalently linked to separate copies of the complementary nucleic acid such that the oligonucleotides form polynucleotide hairpins.

In some embodiments, the complementary nucleic acid is not covalently linked to the oligonucleotides. In some embodiments, the 5' tag sequence is covalently linked to a solid support bead.

In some embodiments, the method is performed in partitions. In some embodiments, the partitions on average comprise 1-3 solid support beads. In some embodiments, the partitions are droplets within an emulsion.

In some embodiments, the method further comprises, following the extending, combining contents of the partitions into a bulk reaction mixture.

In some embodiments, the complementary nucleic acid comprises one or more nucleotide that is incompatible with the strand-displacing polymerase. In some embodiments, one or more nucleotide is one or more uracil. In some embodiments, the one or more nucleotide is biotinylated. In some embodiments, biotinylated nucleotides are bound to streptavidin.

In some embodiments, the strand-displacing polymerase is a phi29 polymerase.

In some embodiments, the random sequence is 4-10 nucleotides long.

In some embodiments, the barcode sequence is 8-50 nucleotides long.

In some embodiments, the intervening sequence is 6-40 nucleotides long.

In some embodiments, the method comprises providing the sample DNA encapsulated in a hydrogel bead, localizing the hydrogel bead in a droplet with at least one of the oligonucleotide, and releasing the sample DNA from the hydrogel thereby contacting the oligonucleotide to the sample DNA. In some embodiments, the sample DNA in the hydrogel consists of DNA from one or more cell. In some embodiments, the method comprises: encapsulating one or more cell in the hydrogel bead, lysing the one or more cell and optionally contacting the lysed cell with one or more proteinase; and separating from the hydrogel beads products of cell lysis that diffuse from the hydrogel bead.

In some embodiments, the method comprises denaturing sample DNA encapsulated by the hydrogel bead. In some embodiments, the method further comprises hybridizing the denatured DNA with random oligonucleotides to maintain the denatured DNA.

In some embodiments, the method comprises encapsulating the hydrogel beads in separate aqueous partitions, rendering the hydrogel beads into solution within the partitions, and then performing the extending in the aqueous partitions. In some embodiments, the partitions are droplets.

In some aspects, a method of generating a partially double-stranded oligonucleotide is provided. In some embodiments, the method comprises, providing a solid support bead covalently linked to a 5' end of an oligonucleotide, the oligonucleotide comprising in the following order: a 3' random sequence of at least four contiguous nucleotides, a consensus universal sequence, and a barcode sequence; annealing an oligonucleotide primer to the consensus universal sequence; and extending the annealed oligonucleotide primer with a polymerase in a template-dependent manner to generate a 2nd strand nucleic acid that is complementary to the consensus universal sequence and barcode sequence, thereby generating a partially double-stranded oligonucleotide with one strand covalently-linked to the solid support bead and having a single-stranded 3' random sequence.

In some embodiments, the oligonucleotide further comprises an intervening sequence. In some embodiments, the barcode sequence is discontinuous and the intervening sequence is between two or more portions of the barcode sequence.

In some embodiments, the oligonucleotide further comprises a 5' tag sequence.

In some embodiments, the extending is performed in the presence of dUTPs such that uracils are incorporated into the 2nd strand nucleic acid. In some embodiments, the dUTPs are biotinylated such that the uracils are incorporated into the 2nd strand nucleic acid are biotinylated. In some embodiments, the method further comprises contacting the 2nd strand nucleic acid with streptavidin.

In some embodiments, the random sequence is 4-10 nucleotides long. In some embodiments, the barcode sequence is 8-50 nucleotides long. In some embodiments, the intervening sequence is 6-40 nucleotides long.

In some aspects, a plurality of oligonucleotides of different sequence are provided. In some embodiments, each oligonucleotide is covalently linked to a separate solid support bead, each oligonucleotide comprising a 3' random sequence of at least four contiguous nucleotides, a barcode sequence, and optionally an intervening sequence, wherein the oligonucleotides differ by having different 3' random sequences, each oligonucleotide annealed to a complementary nucleic acid that is complementary to the barcode sequence, intervening sequence, or both the barcode sequence and the intervening sequence, wherein the complementary nucleic acid is not complementary to the 3' random sequence, leaving the 3' random sequence to be single-stranded.

In some embodiments, the plurality comprises at least 25 different oligonucleotides having different random sequences.

In some embodiments, the oligonucleotides further comprise a 5' tag sequence.

In some embodiments, the tag sequence is 2-40 nucleotides long.

In some embodiments, the oligonucleotides lack the intervening sequence and the complementary nucleic acid is complementary to the barcode sequence, or at least a 6 nucleotide contiguous portion thereof.

In some embodiments, the barcode sequence is unique for each solid support bead.

In some embodiments, the barcode sequence is discontinuous and the intervening sequence is between two or more portions of the barcode sequence.

In some embodiments, wherein the complementary nucleic acid does not comprise a sequence complementary to the barcode sequence.

In some embodiments, the oligonucleotides are covalently linked to separate copies of the complementary nucleic acid such that the oligonucleotides form polynucleotide hairpins.

In some embodiments, the complementary nucleic acid is not covalently linked to the oligonucleotides.

In some embodiments, the complementary nucleic acid comprises one or more nucleotide that is incompatible with a strand-displacing polymerase In some embodiments, the one or more nucleotide is a uracil. In some embodiments, the one or more nucleotide biotinylated and bound to streptavidin.

In some embodiments, the random sequence is 4-10 nucleotides long. In some embodiments, the barcode sequence is 8-50 nucleotides long. In some embodiments, the intervening sequence is 6-40 nucleotides long. In some embodiments, the wherein the random sequence is 4-10 nucleotides long.

DETAILED DESCRIPTION OF THE INVENTION

Introduction

Figure 1:
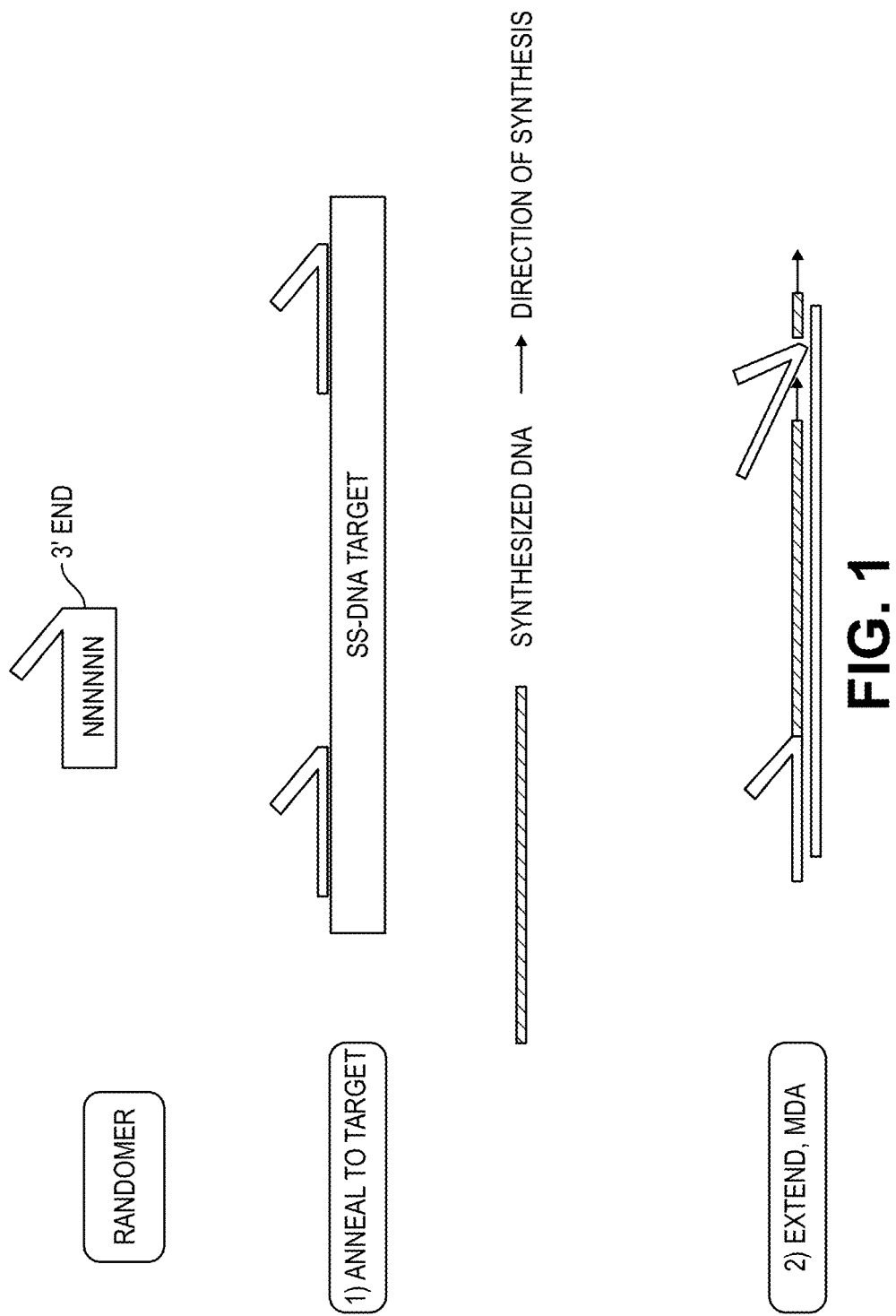
FIG. 1 depicts multiple displacement amplification (MDA) with short randomers.
Figure 2:
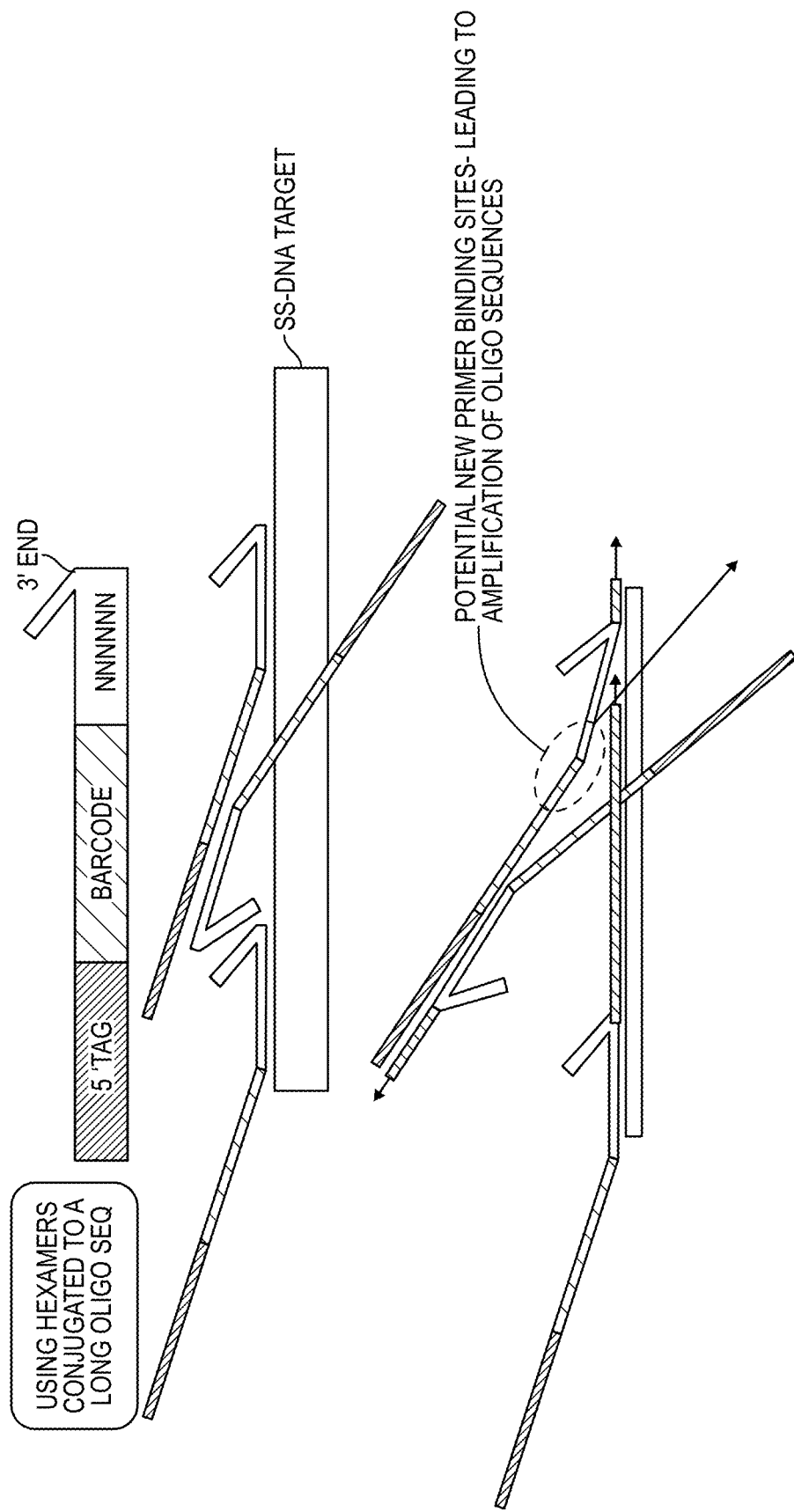
FIG. 2 depicts MDA with barcoded primers having random 3' ends. The bottom section of the figure shows how the longer oligonucleotide primers result in potential new primer binding sites resulting in undesirable spurious amplification of the oligonucleotide sequences themselves.

The inventors have discovered methods and compositions that are useful for performing MDA with barcoded randomized primers while preventing potential self-priming issues that can occur when longer primers are used. For example, while simple hexamers are too short to create significant self-priming products, longer primers that in addition to random sequences have additional 5' sequences such as barcode sequences, 5' tags, or other sequences, can result in significant undesired side-products formed when the randomized 3' ends of the primers use each other as templates.

To address this problem the inventors have discovered a complementary sequence can be provided for the barcoded randomized primers to block self-priming. The complementary sequence can be covalently linked to the barcoded randomized primers (e.g., as a hairpin) or can be a separate oligonucleotide that is not covalently linked to the barcoded randomized primers. Use of the barcoded randomized primers and the complementary sequences in MDA will result in desired MDA products with greatly reduced background of undesired self-priming products.

As noted herein, MDA involves the use of randomized primers to anneal at random locations in DNA, thereby allowing for extension products that comprise the randomized primer sequence and a 3' sequence that is complementary to the DNA. Provided herein are barcoded randomized primers. These primers, also referred to as oligonucleotides, comprise at least a randomized sequence (also referred to as a "random sequence") at the 3' end and a barcode sequence. The randomized sequence can be fully or partially random, and can be of sufficient length to achieve the level of random priming desired for a particular target DNA. In some embodiments, the randomized sequence is at least 4 nucleotides long, for example in some embodiments, the randomized sequence is 4-10 nucleotides long, e.g., 6 nucleotides long. In some embodiments, the randomized sequence is longer than 10 nucleotides, for example between 10-20 nucleotides in length.

In their most simple form, the oligonucleotides described herein comprise only a barcode and a random sequence. Alternatively, as described further below, the oligonucleotides can include additional sequences, including but not limited to, an intervening sequence, a 5' tag sequence, a consensus sequence, or other sequences.

As used herein a "barcode" is a short nucleotide sequence (e.g., at least about 4, 6, 8, 10, or 12, nucleotides long) that identifies a molecule to which it is conjugated. The barcodes can be one contiguous sequence or two or more noncontiguous subsequences. Barcodes can be used, e.g., to identify molecules in a partition or a bead to which an oligonucleotide is attached. In some embodiments, a bead-specific barcode is unique for that bead as compared to barcodes in oligonucleotides linked to other beads. In another example, a nucleic acid from each cell can be distinguished from nucleic acid of other cells due to the unique "cellular barcode." Such partition-specific, cellular, or bead barcodes can be generated using a variety of methods. In some cases, the partition-specific, cellular, or particle barcode is generated using a split and mix (also referred to as split and pool) synthetic scheme, for example as described in WO2015/200541. More than one type of barcodes can in some embodiments be in the oligonucleotides described herein.

In some embodiments, the barcode uniquely identifies the molecule to which it is conjugated. These types of barcodes are sometimes referred to as "unique molecular identifiers" or "UMIs". In still other examples, primers can be utilized that contain "partition-specific barcodes" unique to each partition, and "molecular barcodes" unique to each molecule. After barcoding, partitions can then be combined, and optionally amplified, while maintaining "virtual" partitioning based on the particular barcode. Thus, e.g., the presence or absence of a target nucleic acid comprising each barcode can be counted or tracked (e.g. by sequencing) without the necessity of maintaining physical partitions.

The length of the barcode sequence determines how many unique barcodes can be differentiated. For example, a 1 nucleotide barcode can differentiate 4, or fewer, different samples or molecules; a 4 nucleotide barcode can differentiate $4^4$ or 256 samples or less; a 6 nucleotide barcode can differentiate 4096 different samples or less; and an 8 nucleotide barcode can index 65,536 different samples or less.

Barcodes are typically synthesized and/or polymerized (e.g., amplified) using processes that are inherently inexact. Thus, barcodes that are meant to be uniform (e.g., a cellular, particle, or partition-specific barcode shared amongst all barcoded nucleic acid of a single partition, cell, or bead) can contain various N-1 deletions or other mutations from the canonical barcode sequence. Thus, barcodes that are referred to as "identical" or "substantially identical" copies can in some embodiments include barcodes that differ due to one or more errors in, e.g., synthesis, polymerization, or purification errors, and thus can contain various N-1 deletions or other mutations from the canonical barcode sequence. However, such minor variations from theoretically ideal barcodes do not interfere with the high-throughput sequencing analysis methods, compositions, and kits described herein. Therefore, as used herein, the term "unique" in the context of a particle, cellular, partition-specific, or molecular barcode encompasses various inadvertent N-1 deletions and mutations from the ideal barcode sequence. In some cases, issues due to the inexact nature of barcode synthesis, polymerization, and/or amplification, are overcome by oversampling of possible barcode sequences as compared to the number of barcode sequences to be distinguished (e.g., at least about 2-, 5-, 10-fold or more possible barcode sequences). For example, 10,000 cells can be analyzed using a cellular barcode having 9 barcode nucleotides, representing 262,144 possible barcode sequences. The use of barcode technology is well known in the art, see for example Katsuyuki Shiroguchi, et al. Proc Natl Acad Sci USA., 2012 Jan. 24; 109(4):1347-52; and Smith, A M et al., Nucleic Acids Research Can 11, (2010). Further methods and compositions for using barcode technology include those described in U.S. 2016/0060621.

Figure 3:
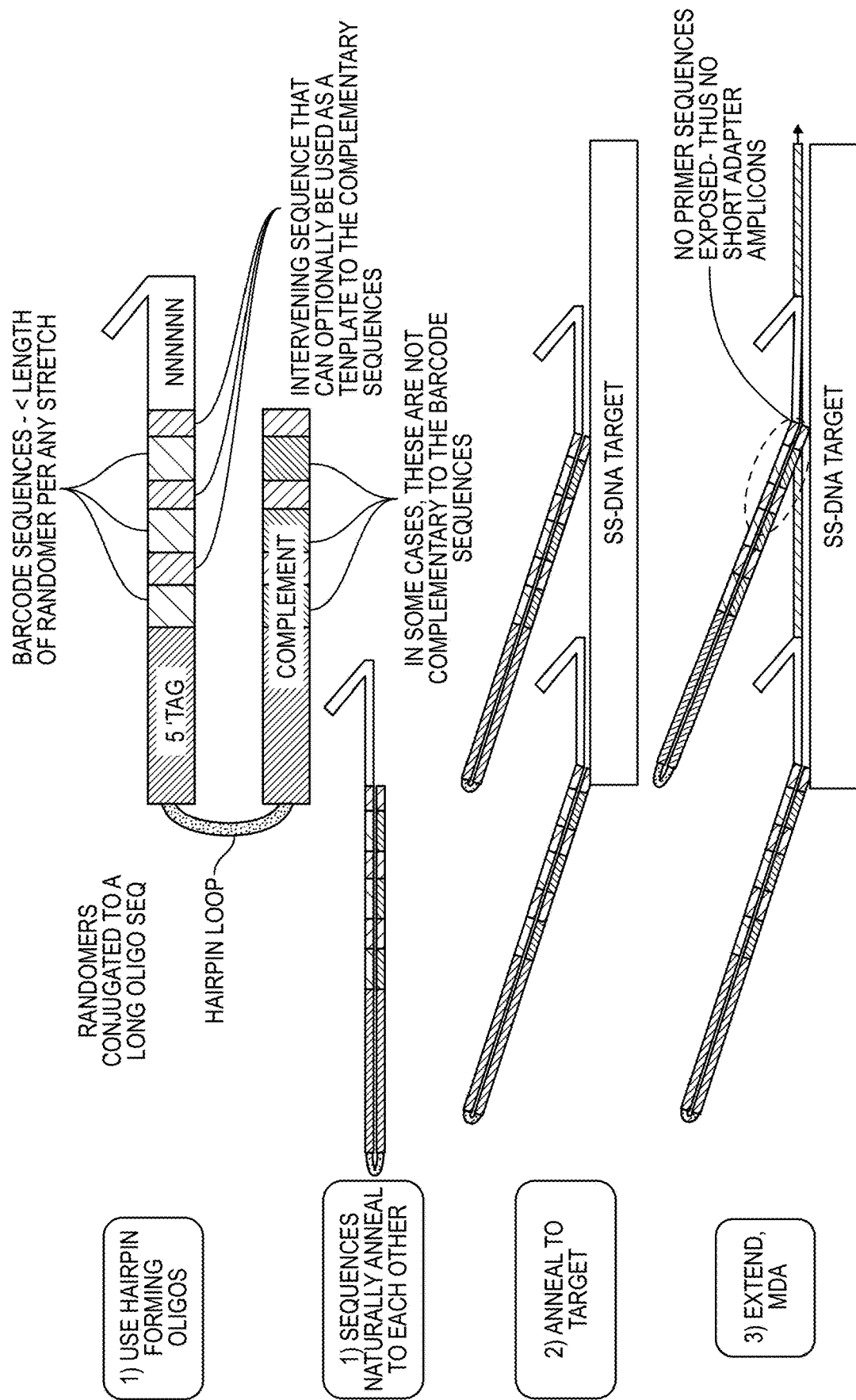
FIG. 3 depicts a solution to the problem in FIG. 2. Specifically, providing a barcoded MDA oligonucleotide having a complementary sequence protects against spurious amplification in which the oligonucleotide acts as a template.
Figure 4:
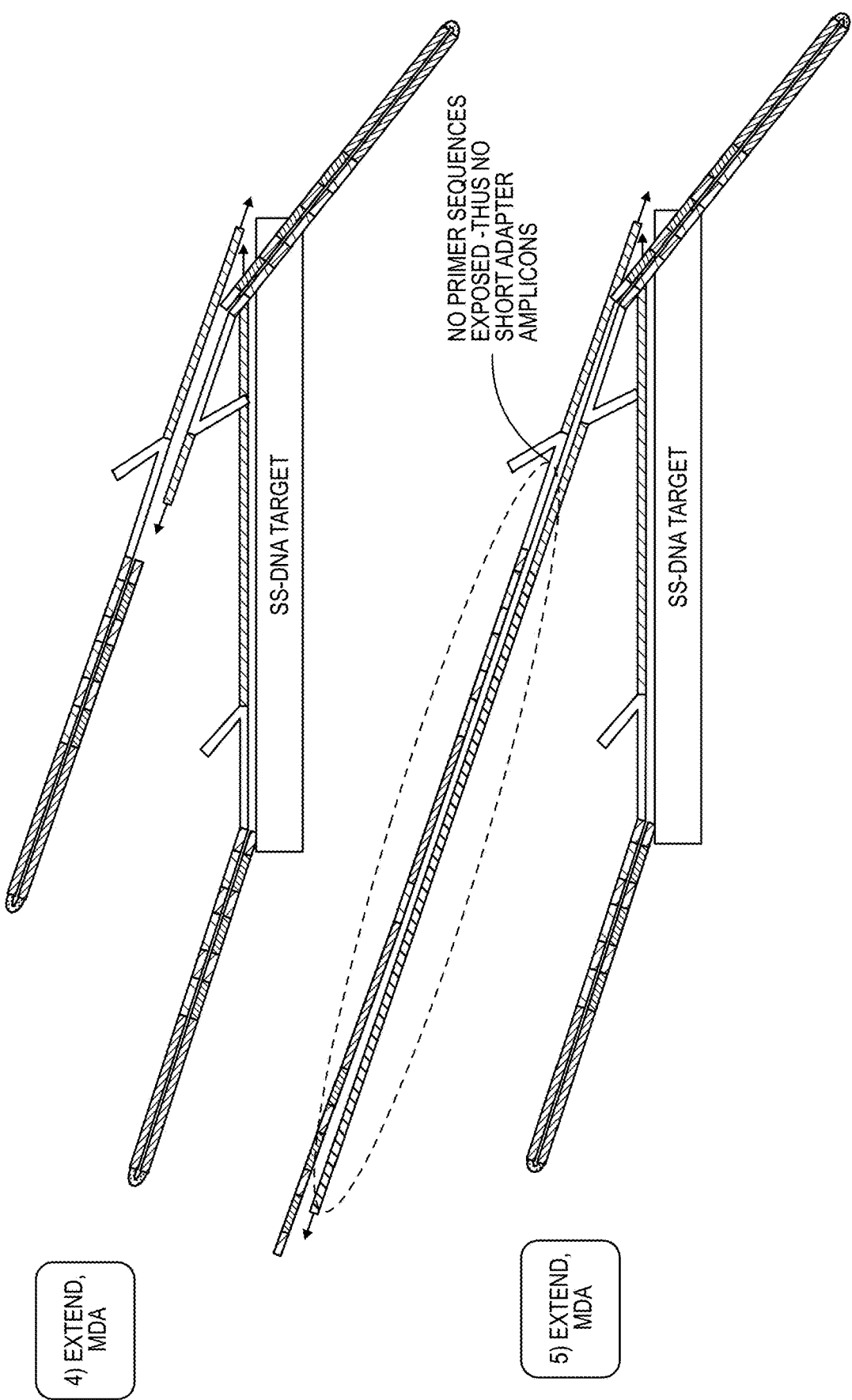
FIG. 4 continues the method of FIG. 5 showing the subsequent steps of an MDA reaction. Specifically as barcoded primers anneal to nascent single stranded DNA resulting in DNA synthesis, previously incorporated barcoded MDA oligonucleotide complementary sequences are displaced leading to the full synthesis of the adapter.

In some embodiments, the oligonucleotides comprise what is referred to herein an "intervening sequence." An intervening sequence is an sequence that can be (1) between the barcode and the random sequence, (2) 5' to the barcode sequence, or (3) a sequence that divides the barcode into two or more barcode portions, wherein the barcode portions are separated by an intervening sequence. FIG. 3 depicts certain embodiments of intervening sequences. The intervening sequence itself can occur in separate (e.g., 2, 3, 4 or more) parts, for example, such that a portion of the oligonucleotide is laid out as follows: 5' first barcode portion-first intervening sequence portion-second barcode portion-second intervening portion sequence-remainder of oligonucleotide. The intervening sequence can be of any sequence that does not inhibit primer function. In some embodiments, the intervening sequencing is 1-40 nucleotides, e.g., 2-20 nucleotides long. As discussed further below, in some embodiments, the complementary sequence is complementary to at least the intervening sequence.

In some embodiments, the oligonucleotides comprise a further 5' sequence such as a tag sequence or other sequence as desired. The tag sequence can be long enough to support new priming events (e.g., at least 10 nt long but in some embodiments, not more than 40). In some embodiments, the tag sequence is a sequencing primer sequence (e.g., as used in Illumina sequencing, e.g., the RD1 portion of Illumina TruSeq). Alternatively, if the sequencing primer sequence is provided in the intervening sequences above, then the tag sequence could be the P5 or P7 grafting sequences. The RD1, P5 and P7 sequences are provided below:

RD1
ACACTCTTTCCCTACACGACGCTCTTCCGATCT (SEQ ID NO: 1)

P5
AATGATACGGCGACCACCGAGATCT (SEQ ID NO: 2)

P7
CAAGCAGAAGACGGCATACGAGAT (SEQ ID NO: 3)

In some embodiments as described herein, the oligonucleotides are linked (covalently or non-covalently) to a solid support, e.g., a bead. The bead can be any particle or bead having a solid support surface. In some embodiments, the size of the beads, i.e., the diameters of the various size beads, can be the range from 0.1 µm to 100 µm. In some embodiments, the range is 1 µm to 30 µm. Solid supports suitable for particles include controlled pore glass (CPG)(available from Glen Research, Sterling, Va.), oxalyl-controlled pore glass (See, e.g., Alul, et al., Nucleic Acids Research 1991, 19, 1527), TentaGel Support—an aminopolyethyleneglycol derivatized support (See, e.g., Wright, et al., Tetrahedron Letters 1993, 34, 3373), polystyrene, Poros (a copolymer of polystyrene/divinylbenzene), or reversibly cross-linked acrylamide. Many other solid supports are commercially available and amenable to the present invention. In some embodiments, the bead material is a polystyrene resin or poly(methyl methacrylate) (PMMA). The bead material can be metal. The term "bead" encompasses microparticles.

In some embodiments, the bead is a hydrogel bead. In some cases, the hydrogel is in sol form. In some cases, the hydrogel is in gel form. An exemplary hydrogel is an agarose hydrogel. Other hydrogels include, but are not limited to, those described in, e.g., U.S. Pat. Nos. 4,438,258; 6,534,083; 8,008,476; 8,329,763; U.S. Patent Appl. Nos. 2002/0,009,591; 2013/0,022,569; 2013/0,034,592; and International Patent Publication Nos. WO/1997/030092; and WO/2001/049240.

The solid support surface of the bead can be modified to include a linker for attaching barcode oligonucleotides. The linkers may comprise a cleavable moiety. Non-limiting examples of cleavable moieties include a disulfide bond, a dioxyuridine moiety, and a restriction enzyme recognition site. Numerous methods for covalently linking an oligonucleotide to one or more hydrogel matrices are known in the art. As but one example, aldehyde derivatized agarose can be covalently linked to a 5'-amine group of a synthetic oligonucleotide. In some embodiments, the oligonucleotide configured to link the hydrogel to the barcode is conjugated to a high molecular weight (e.g., at least about 5, 10, 15, 20, 25, 30, 35, 40, 50 kDa, or more) polymer that can be sterically constrained within a gel form hydrogel matrix. For example, the oligonucleotide can be conjugated to a high molecular weight linear or branched polyacrylamide. As another example, the oligonucleotide can be conjugated to a high molecular weight nucleic acid. The high molecular weight polymer oligonucleotide conjugate (e.g., linear polyacrylamide oligonucleotide conjugate) can be incorporated into a hydrogel matrix by mixing with sol hydrogel and hardening the hydrogel into gel form. In some cases, the plurality of the partitions contain an oligonucleotide conjugated to a high molecular weight linear or branched polyacrylamide, a hydrogel in sol form, and a bifunctional barcode template containing a unique partition-specific barcode. Other high molecular weight polymers are suitable for conjugation with an oligonucleotide and encapsulation into a hydrogel. Exemplary polymers include, but are not limited to, dextrans, chitosan, styrenated gelatin, hyaluronic acid, alginate, gelatin, polyethylene glycols, and derivatives thereof.

In some cases, the oligonucleotide is conjugated into a linear polyacrylamide by forming a reaction mixture containing one or more acrydite-oligonucleotides and a plurality of acrylamide monomers and polymerizing the reaction mixture to generate a linear polyacrylamide-oligonucleotide conjugate. The reaction can be performed to generate a plurality of linear polyacrylamide-oligonucleotide conjugates. The mean number of oligonucleotides incorporated into the linear polyacrylamide molecules can be controlled by altering the reaction conditions. For example the following non-limiting reaction conditions can be altered to control the average number of incorporated oligonucleotides: pH; temperature; incident light intensity; time of the polymerization reaction; or concentration of oligonucleotide, acrylamide monomer, catalyst (e.g., TEMED), or initiator (e.g., riboflavin or ammonium persulfate).

As noted above, the oligonucleotides described herein are provided with a complementary sequence that is at least partly complementary to the oligonucleotide and thus blocks mis-priming events in which primers would otherwise use one primer itself as a template. The complementary sequence will comprise sufficient number of complementary nucleotides such that the complementary sequence hybridizes to the oligonucleotide under the conditions of the MDA assay. The complementary sequence need not be complementary to the full-length of the oligonucleotide sequence, and in many cases can be only partially complementary (e.g., complementary to at least 98%, 95%, 90%, 85%, 80%, 70% of the oligonucleotide sequence) to the oligonucleotide. In some embodiments, the oligonucleotides comprise an intervening sequence as described above and the complementary sequence is complementary at least to some or all of the intervening sequence. In some embodiments, the complementary sequence comprises one or more sequence that is complementary to all or part (e.g., at least 50%, 60%, 70%, 80%, 90%) of the barcode. In general, the complementary sequence is not complementary to the 3' random sequence of the oligonucleotide, leaving the 3' end single-stranded even in the presence of the complementary sequence, and thus available to prime in the MDA reaction.

The complementary sequence can be linked to the oligonucleotide sequence such that the oligonucleotide sequence and the complementary sequence form a "hairpin." See, for example, FIG. 3. For example, in some embodiments, the complementary sequence is at or near the 5' end of the oligonucleotide sequence itself, with a loop nucleotide sequence between the randomer, barcode and other 5' tag sequence and the complementary sequence.

Alternatively, the complementary sequence is not covalently linked to the oligonucleotide sequence and instead is a separate molecule that can hybridize to the oligonucleotide under the MDA conditions.

Figure 8:
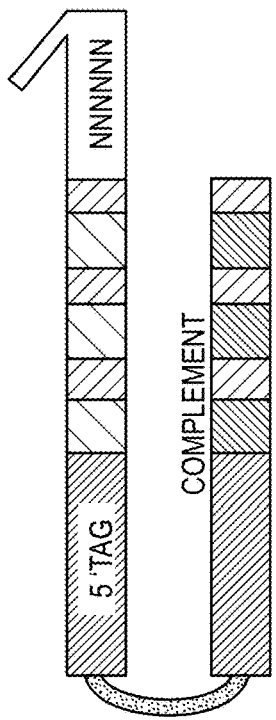
FIG. 8 depicts a method of generating a complementary sequence from barcoded oligonucleotides having a 3' end sequence by using a "consensus universal sequence" that can act as a primer extension site to generate the complementary sequence.
Figure 8:
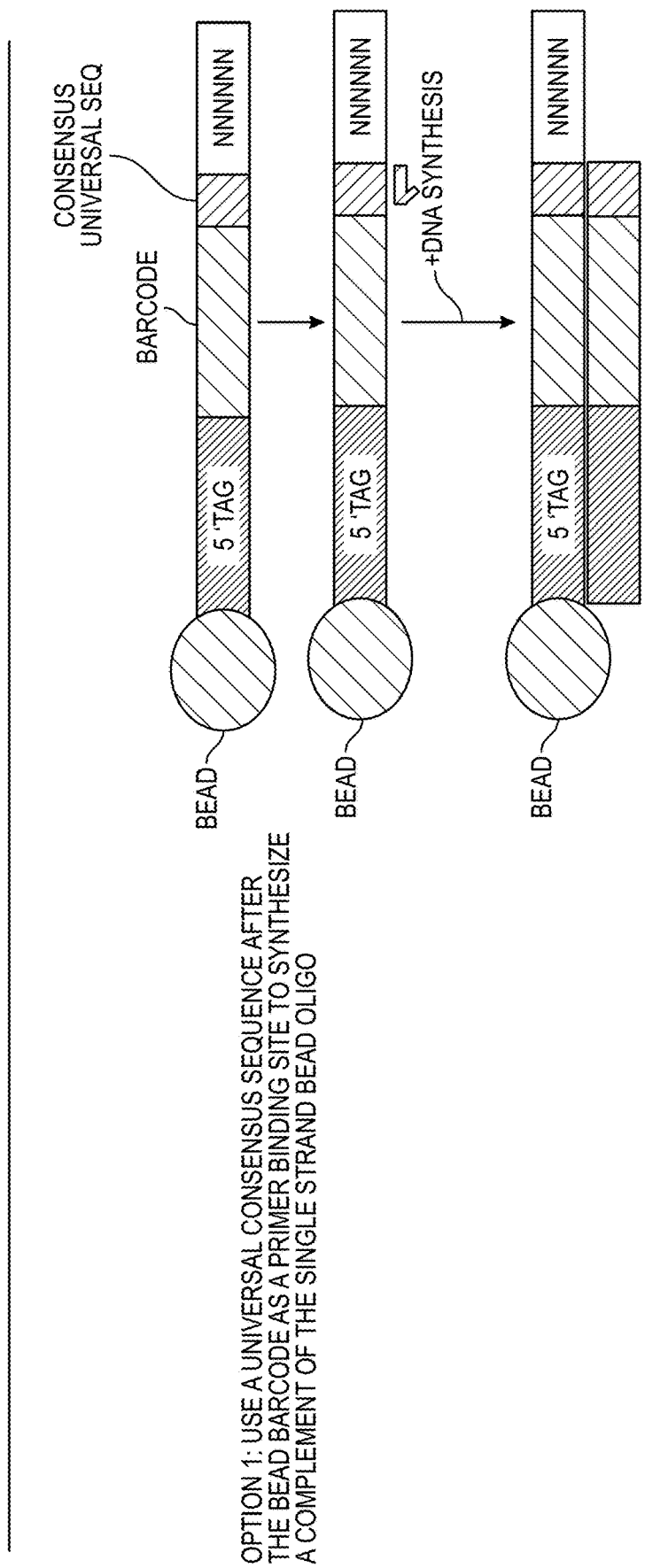

The oligonucleotide sequence and complementary sequence can be generated by synthesis or other methods as desired. Some methods for generating separate complementary sequences not covalently linked to the oligonucleotide sequence in FIGS. 8-12. For example, as depicted in FIG. 8, in some embodiments, the oligonucleotide sequence can include a "universal" sequence directly 5' of the random sequence (in FIG. 8 it is referred to as a "consensus universal seq") that can be a site to which a primer anneals allowing for DNA synthesis of the complementary sequence. For example, in some embodiments, during synthesis of barcode oligos the annealed primer can be extended with a polymerase in a template-dependent manner to generate a $2^{nd}$ strand nucleic acid that is complementary to the universal sequence and barcode sequence, thereby generating a partially double-stranded oligonucleotide with one strand covalently-linked to the solid support bead and having a single-stranded 3' random sequence.

Figure 9:
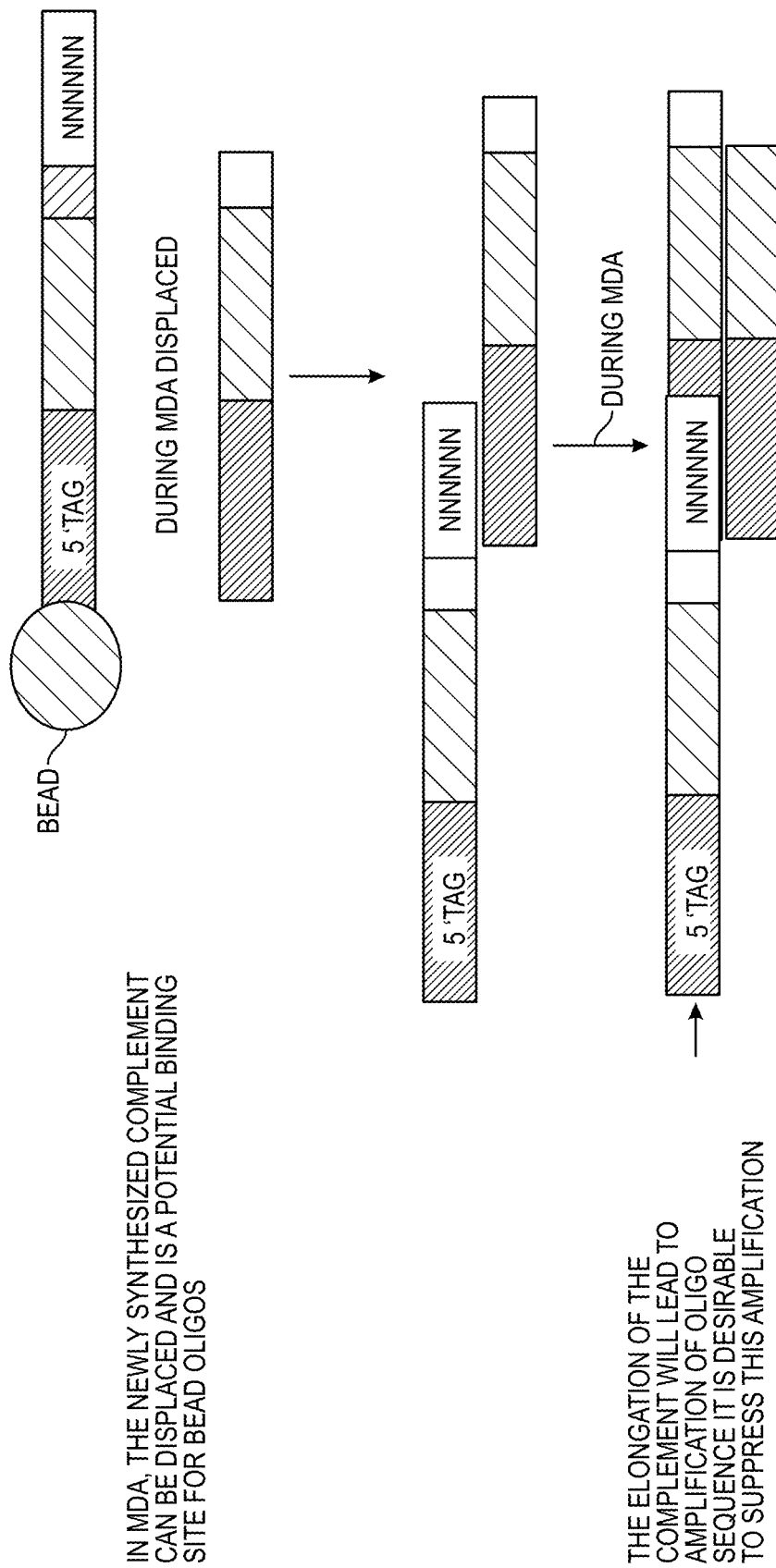
FIG. 9 depicts how the complementary sequence can also potentially be a source of spurious amplification.
Figure 10:
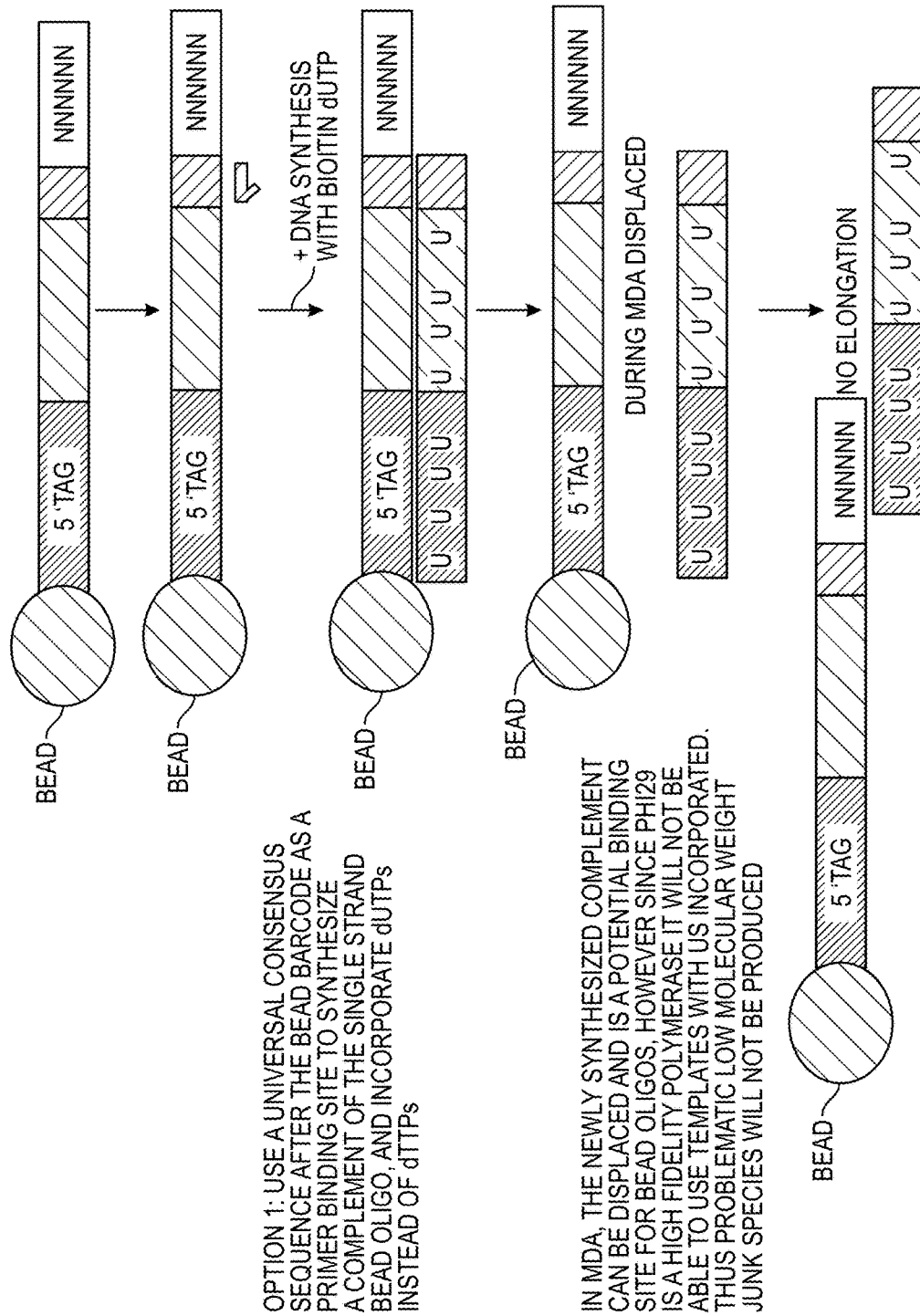
FIG. 10 describes embodiments for synthesis of complementary sequences that will reduce the availability of the complementary sequence as a source of spurious amplification. For instance, incorporating UTPs into the complementary sequence will reduce the ability of phi29 or other displacing polymerases from using the complementary sequence as a template.
Figure 11:
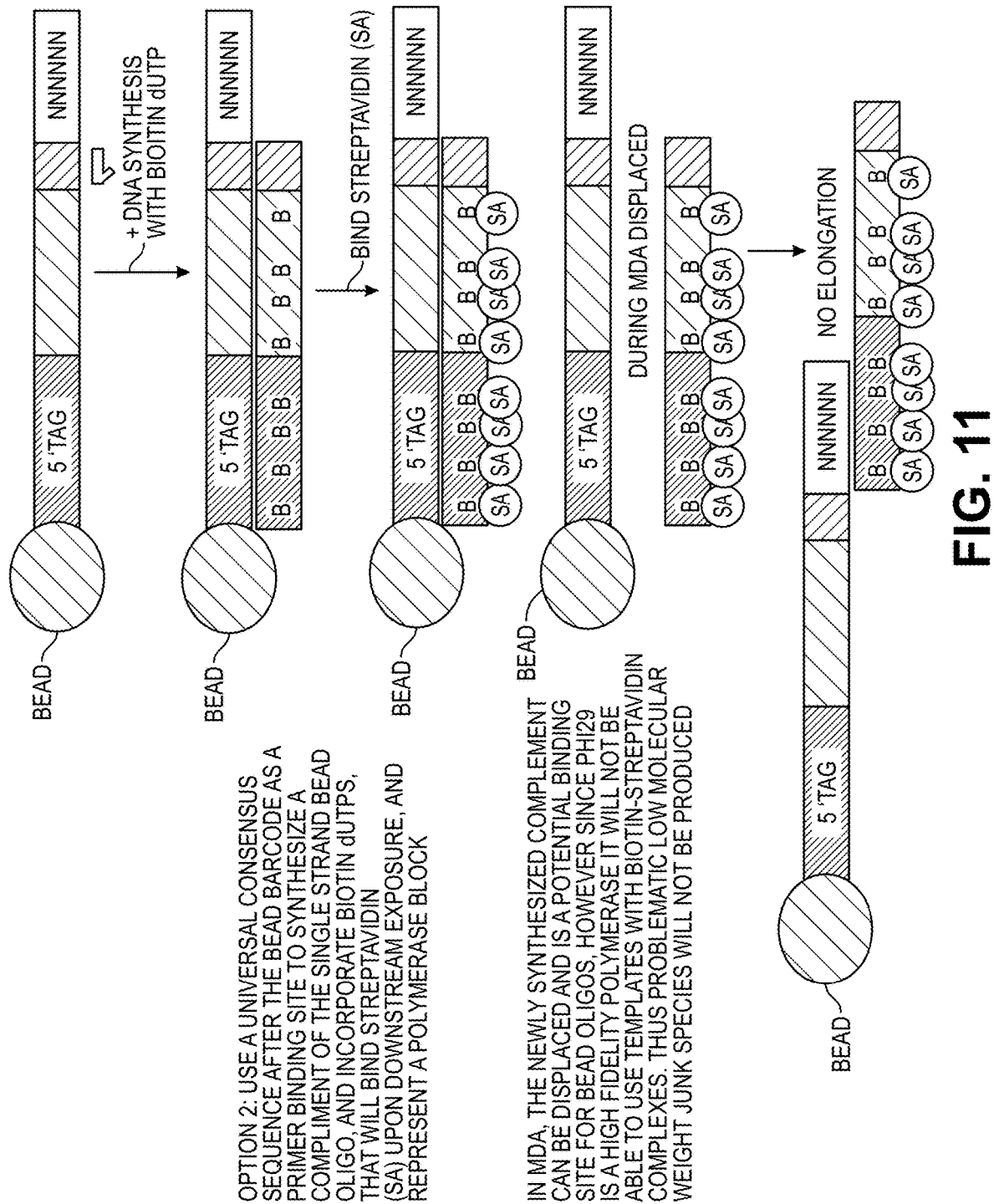
FIG. 11 describes embodiments for synthesis of complementary sequences that will reduce the availability of the complementary sequence as a source of spurious amplification. For instance, incorporating biotinylated nucleotides into the complementary sequence and binding the incorporated biotins with streptavidin will reduce the ability of phi29 or other displacing polymerases from using the complementary sequence as a template.
Figure 12:
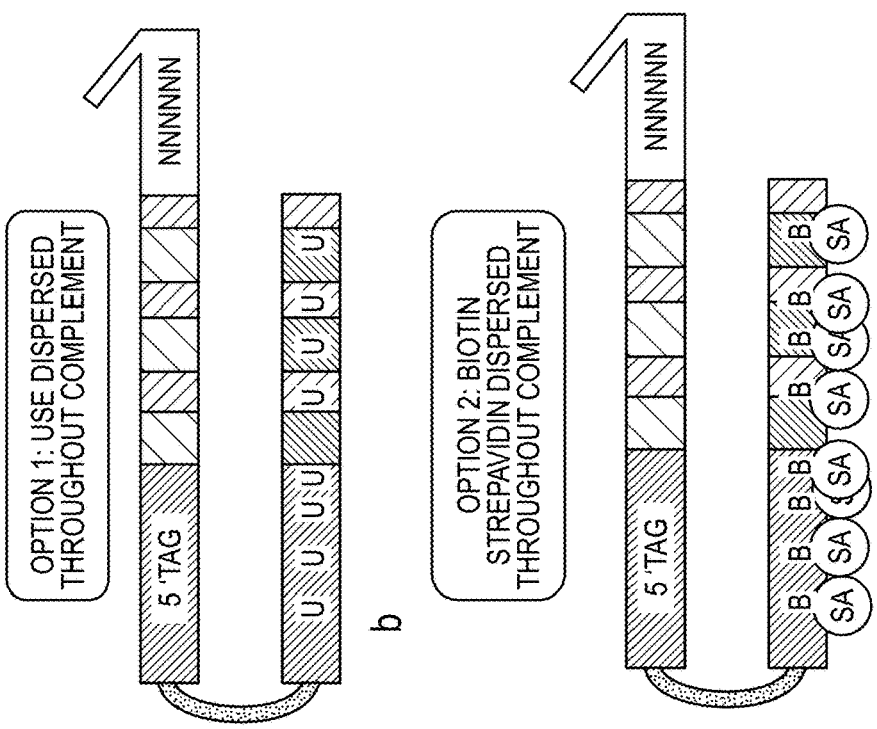
FIG. 12 depicts that the aspects for FIGS. 10-11 can also be introduced into complementary sequences of hairpin oligonucleotides.
Figure 12:
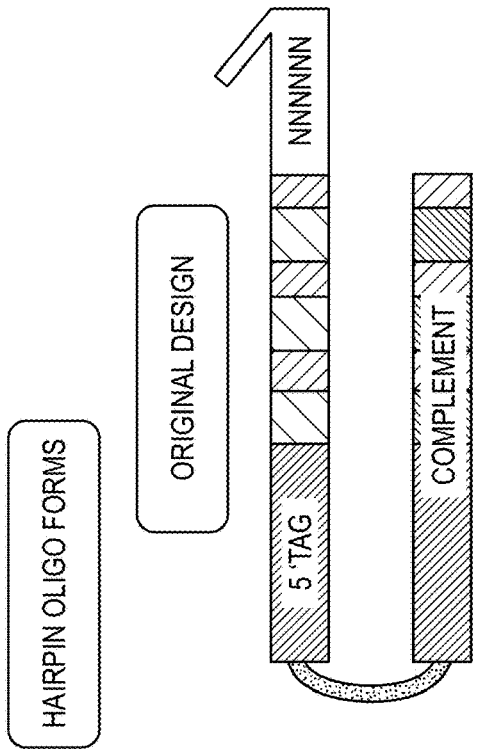

As shown in FIG. 9, in some embodiments, if the complementary sequence is not covalently linked to the oligonucleotide sequence, the complementary sequence itself may inappropriately be used as a template to form mis-priming events. Thus, in some embodiments, it can be desirable to suppress these mis-priming events as well. In some embodiments, such mis-primed products can be suppressed by extending the primer that is complementary to the consensus sequence in a reaction with one or more nucleotide that can be incorporated into the $2^{nd}$ strand but that also is incompatible with the strand displacing polymerase used in the later MDA step. Exemplary nucleotides that are incompatible with a strand displacing polymerase (e.g., phi29) that can be incorporated into the complementary sequence include, but are not limited to, uracils (UTPs) or biotinylated nucleotides. As shown in FIG. 10, the presence of incorporated uracils in the complementary sequence will inhibit polymerase activity from using the complementary sequence as a template. Alternatively, for example as depicted in FIG. 11, if biotinylated nucleotides are introduced into the complementary sequence, streptavidin or other avidin molecules with affinity for biotin can be added before the strand displacing reaction, thereby inhibiting the strand displacing polymerase activity for the complementary strand. As noted in FIG. 12, nucleotides that are incompatible with a strand displacing polymerase can also advantageously be included in the consensus sequence as part of a hairpin to inhibit the reaction from using the complementary sequence as a template during the strand displacement reaction.

Also provided is a plurality of the oligonucleotides as described herein of different sequence each covalently linked to a separate solid support. Each oligonucleotide can comprise a 3' randomer sequence (as described above), a barcode sequence (as described above), and optionally an intervening sequence (as described above), wherein the oligonucleotides differ at least by having different 3' random sequences (i.e., the sequences are different). Each oligonucleotide will be annealed to a complementary sequence as described above. The plurality can include at least 5, 10, 25, 50, 100, or more different oligonucleotides as described above, each linked to a separate solid support.

In some embodiments, small numbers of (e.g., 1-5, 1-4, 1-3, 1-2) or single oligonucleotides, optionally linked to a bead, are in separate partitions. As used herein, the term "partitioning" or "partitioned" refers to separating a sample into a plurality of portions, or "partitions." Partitions are generally physical, such that a sample in one partition does not, or does not substantially, mix with a sample in an adjacent partition. Partitions can be solid or fluid. In some embodiments, a partition is a solid partition, e.g., a microchannel. In some embodiments, a partition is a fluid partition, e.g., a droplet. In some embodiments, a fluid partition (e.g., a droplet) is a mixture of immiscible fluids (e.g., water and oil). In some embodiments, a fluid partition (e.g., a droplet) is an aqueous droplet that is surrounded by an immiscible carrier fluid (e.g., oil). Any type of partition can be used with oligonucleotides and beads described herein.

Methods and compositions for partitioning are described, for example, in published patent applications WO 2010/036,352, US 2010/0173,394, US 2011/0092,373, and US 2011/0092,376, the contents of each of which are incorporated herein by reference in the entirety. The plurality of mixture partitions can be in a plurality of emulsion droplets, or a plurality of microwells, etc.

The mixture partitions can be picowells, nanowells, or microwells. The mixture partitions can be pico-, nano-, or micro-reaction chambers, such as pico, nano, or microcapsules. The mixture partitions can be pico-, nano-, or microchannels.

In some embodiments, the partitions are droplets. In some embodiments, a droplet comprises an emulsion composition, i.e., a mixture of immiscible fluids (e.g., water and oil). In some embodiments, a droplet is an aqueous droplet that is surrounded by an immiscible carrier fluid (e.g., oil). In some embodiments, a droplet is an oil droplet that is surrounded by an immiscible carrier fluid (e.g., an aqueous solution). In some embodiments, the droplets described herein are relatively stable and have minimal coalescence between two or more droplets. In some embodiments, less than 0.0001%, 0.0005%, 0.001%, 0.005%, 0.01%, 0.05%, 0.1%, 0.5%, 1%, 2%, 3%, 4%, 5%, 6%, 7%, 8%, 9% or 10% of droplets generated from a sample coalesce with other droplets. The emulsions can also have limited flocculation, a process by which the dispersed phase comes out of suspension in flakes. In some cases, such stability or minimal coalescence is maintained for up to 4, 6, 8, 10, 12, 24, or 48 hours or more (e.g., at room temperature, or at about 0, 2, 4, 6, 8, 10, or 12° C.). In some embodiments, the droplet is formed by flowing an oil phase through an aqueous sample or reagents.

The oil phase can comprise a fluorinated base oil which can additionally be stabilized by combination with a fluorinated surfactant such as a perfluorinated polyether. In some embodiments, the base oil comprises one or more of a HFE 7500, FC-40, FC-43, FC-70, or another common fluorinated oil. In some embodiments, the oil phase comprises an anionic fluorosurfactant. In some embodiments, the anionic fluorosurfactant is Ammonium Krytox (Krytox-AS), the ammonium salt of Krytox FSH, or a morpholino derivative of Krytox FSH. Krytox-AS can be present at a concentration of about 0.1%, 0.2%, 0.3%, 0.4%, 0.5%, 0.6%, 0.7%, 0.8%, 0.9%, 1.0%, 2.0%, 3.0%, or 4.0% (w/w). In some embodiments, the concentration of Krytox-AS is about 1.8%. In some embodiments, the concentration of Krytox-AS is about 1.62%. Morpholino derivative of Krytox FSH can be present at a concentration of about 0.1%, 0.2%, 0.3%, 0.4%, 0.5%0, 0.6%, 0.7%, 0.8%, 0.9%, 1.0%, 2.0%, 3.0%, or 4.0% (w/w).

In some embodiments, the concentration of morpholino derivative of Krytox FSH is about 1.8%. In some embodiments, the concentration of morpholino derivative of Krytox FSH is about 1.62%.

In some embodiments, the oil phase further comprises an additive for tuning the oil properties, such as vapor pressure, viscosity, or surface tension. Non-limiting examples include perfluorooctanol and 1H,1H,2H,2H-Perfluorodecanol. In some embodiments, 1H,1H,2H,2H-Perfluorodecanol is added to a concentration of about 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 1.25%, 1.50%, 1.75%, 2.0%, 2.25%, 2.5%, 2.75%, or 3.0% (w/w). In some embodiments, 1H,1H,2H,2H-Perfluorodecanol is added to a concentration of about 0.18% (w/w).

In some embodiments, the emulsion is formulated to produce highly monodisperse droplets having a liquid-like interfacial film that can be converted by heating into microcapsules having a solid-like interfacial film; such microcapsules can behave as bioreactors able to retain their contents through an incubation period. The conversion to microcapsule form can occur upon heating. For example, such conversion can occur at a temperature of greater than about 40°, 50°, 60°, 70°, 80°, 90°, or 95° C. During the heating process, a fluid or mineral oil overlay can be used to prevent evaporation. Excess continuous phase oil can be removed prior to heating, or left in place. The microcapsules can be resistant to coalescence and/or flocculation across a wide range of thermal and mechanical processing.

Following conversion of droplets into microcapsules, the microcapsules can be stored at about −70°, −20°, 0°, 3°, 4°, 5°, 6°, 7° 8°, 9° 10°, 15°, 20°, 25°, 30°, 35° or 40° C. In some embodiments, these capsules are useful for storage or transport of partition mixtures. For example, samples can be collected at one location, partitioned into droplets, optionally containing one or more reagent described herein, optionally one or more polymerization reactions can be performed, the partitions can then be heated to perform microencapsulation, and the microcapsules can be stored or transported for further analysis.

In some embodiments, the sample is partitioned into, or into at least, 500 partitions, 1000 partitions, 2000 partitions, 3000 partitions, 4000 partitions, 5000 partitions, 6000 partitions, 7000 partitions, 8000 partitions, 10,000 partitions, 15,000 partitions, 20,000 partitions, 30,000 partitions, 40,000 partitions, 50,000 partitions, 60,000 partitions, 70,000 partitions, 80,000 partitions, 90,000 partitions, 100,000 partitions, 200,000 partitions, 300,000 partitions, 400,000 partitions, 500,000 partitions, 600,000 partitions, 700,000 partitions, 800,000 partitions, 900,000 partitions, 1,000,000 partitions, 2,000,000 partitions, 3,000,000 partitions, 4,000,000 partitions, 5,000,000 partitions, 10,000,000 partitions, 20,000,000 partitions, 30,000,000 partitions, 40,000,000 partitions, 50,000,000 partitions, 60,000,000 partitions, 70,000,000 partitions, 80,000,000 partitions, 90,000,000 partitions, 100,000,000 partitions, 150,000,000 partitions, or 200,000,000 partitions.

In some embodiments, the droplets that are generated are substantially uniform in shape and/or size. For example, in some embodiments, the droplets are substantially uniform in average diameter. In some embodiments, the droplets that are generated have an average diameter of about 0.001 microns, about 0.005 microns, about 0.01 microns, about 0.05 microns, about 0.1 microns, about 0.5 microns, about 1 microns, about 5 microns, about 10 microns, about 20 microns, about 30 microns, about 40 microns, about 50 microns, about 60 microns, about 70 microns, about 80 microns, about 90 microns, about 100 microns, about 150 microns, about 200 microns, about 300 microns, about 400 microns, about 500 microns, about 600 microns, about 700 microns, about 800 microns, about 900 microns, or about 1000 microns. In some embodiments, the droplets that are generated have an average diameter of less than about 1000 microns, less than about 900 microns, less than about 800 microns, less than about 700 microns, less than about 600 microns, less than about 500 microns, less than about 400 microns, less than about 300 microns, less than about 200 microns, less than about 100 microns, less than about 50 microns, or less than about 25 microns. In some embodiments, the droplets that are generated are non-uniform in shape and/or size.

In some embodiments, the droplets that are generated are substantially uniform in volume. For example, the standard deviation of droplet volume can be less than about 1 picoliter, 5 picoliters, 10 picoliters, 100 picoliters, 1 nL, or less than about 10 nL. In some cases, the standard deviation of droplet volume can be less than about 10-25% of the average droplet volume. In some embodiments, the droplets that are generated have an average volume of about 0.001 nL, about 0.005 nL, about 0.01 nL, about 0.02 nL, about 0.03 nL, about 0.04 nL, about 0.05 nL, about 0.06 nL, about 0.07 nL, about 0.08 nL, about 0.09 nL, about 0.1 nL, about 0.2 nL, about 0.3 nL, about 0.4 nL, about 0.5 nL, about 0.6 nL, about 0.7 nL, about 0.8 nL, about 0.9 nL, about 1 nL, about 1.5 nL, about 2 nL, about 2.5 nL, about 3 nL, about 3.5 nL, about 4 nL, about 4.5 nL, about 5 nL, about 5.5 nL, about 6 nL, about 6.5 nL, about 7 nL, about 7.5 nL, about 8 nL, about 8.5 nL, about 9 nL, about 9.5 nL, about 10 nL, about 11 nL, about 12 nL, about 13 nL, about 14 nL, about 15 nL, about 16 nL, about 17 nL, about 18 nL, about 19 nL, about 20 nL, about 25 nL, about 30 nL, about 35 nL, about 40 nL, about 45 nL, or about 50 nL.

Sample DNA refers to DNA that is to be detected, sequenced, or otherwise characterized from a sample of any type. Sample DNA can be derived from one or more cell, and can be, for example, genomic DNA or cDNA. The DNA can be naturally-occurring (e.g., primary copies from a cell) or can be for example, amplified DNA. In some embodiments, the DNA can be chimeric (e.g., DNA including heterologous adaptor sequence at one or both ends). Such cells can be primary cells or cultured cells. In some embodiments, the DNA is amplified from a biological sample. The DNA can be from viruses, prokaryotes, or eukaryotes (including but not limited to animals (including but not limited to humans), plants, or fungi.

Methods

Methods of using the described oligonucleotides are also provided. In some embodiments, the described oligonucleotides are used as primers in a multiple displacement amplification (MDA) reaction. MDA is a non-PCR-based isothermal method based on the annealing of primers having random 3' ends to denatured DNA, followed by strand-displacement synthesis at constant temperature (see, e.g., Blanco et al. *J. Biol. Chem.* 1989, 264, 8935-8940). The reaction can be catalyzed by enzymes such as, but not limited to, the Phi29 DNA polymerase or the large fragment of the Bst DNA polymerase. In some embodiments, an oligonucleotide as described herein (i.e., having a 3' randomized sequence, a barcode, optionally an intervening sequence, and linked or separate a complementary sequence as described herein) is contacted to denatured target DNA to anneal at least the randomized sequence to the target DNA and then is extended in a template-dependent manner with a strand-displacing polymerase. Conditions for performing MDA can be found in, e.g., U.S. Pat. No. 6,977,148. Certain steps of MDA using an embodiment of the oligonucleotides described herein are provided in FIG. 3, depicting for example annealing of the oligonucleotides to the sample (target) DNA and subsequent extension of the oligonucleotides with a polymerase, thereby generating random primer extension products that include a barcode. Extension products from the MDA recation can subsequently be sequenced using any desired sequencing technology.

In some embodiments, prior to contact with the oligonucleotides described herein, the sample DNA can be annealed to short denatured random oligonucleotides (e.g., of 5-25 nucleotides in length). The annealed oligonucleotides can be used to prevent complementary strands of the sample DNA from completely reannealing if subsequently submitted to non-denaturing (e.g., cooler) conditions. Excess, non-annealing, random oligonucleotides can be removed, if desired, from the sample DNA, for example using a size-selection column. The denatured sample DNA can then be mixed with the oligonucleotides as described herein (i.e., having a 3' randomized sequence, a barcode, optionally an intervening sequence, and linked or separate a complementary sequence as described herein, and optionally linked to a bead) and a MDA reaction can be performed.

Figure 5:
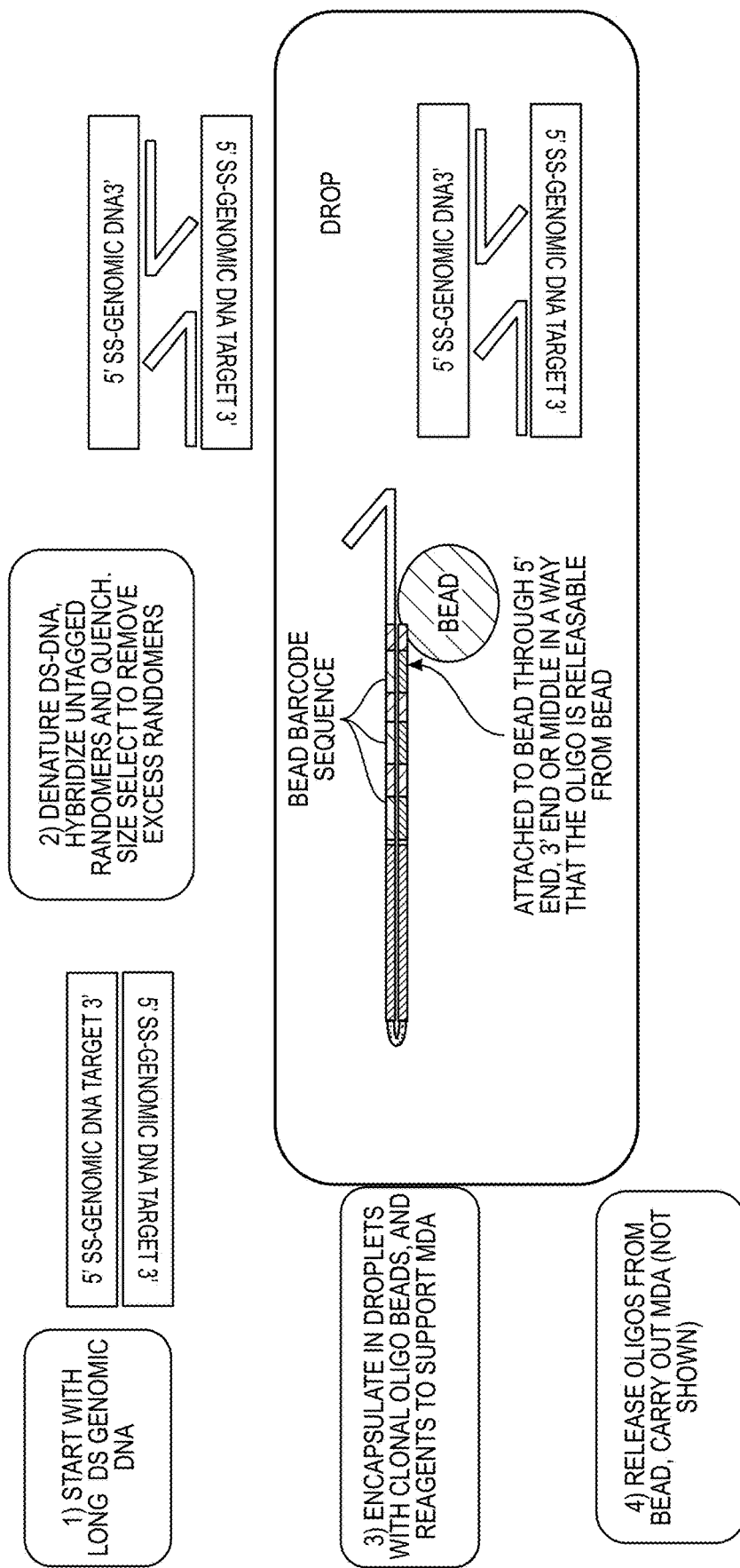
FIG. 5 depicts an MDA method in which dsDNA is denatured and hybridized with random primers, encapsulated into droplets, and amplified using a barcoded oligonucleotide having a free random 3' end and a complementary sequence that protects from spurious amplification of the oligonucleotide itself.

In some embodiments, the oligonucleotide and DNA sample can be combined and partitioned together. The oligonucleotide can be released from the bead, if present, in the partition, and MDA can subsequently be performed within the partitions, thereby generating within the partitions barcoded MDA extension products. The partitions can subsequently be combined and the extension products can be characterized (e.g., sequenced), with each partition being represented by a different barcode. Aspects of this method are depicted in FIG. 5.

Figure 6:
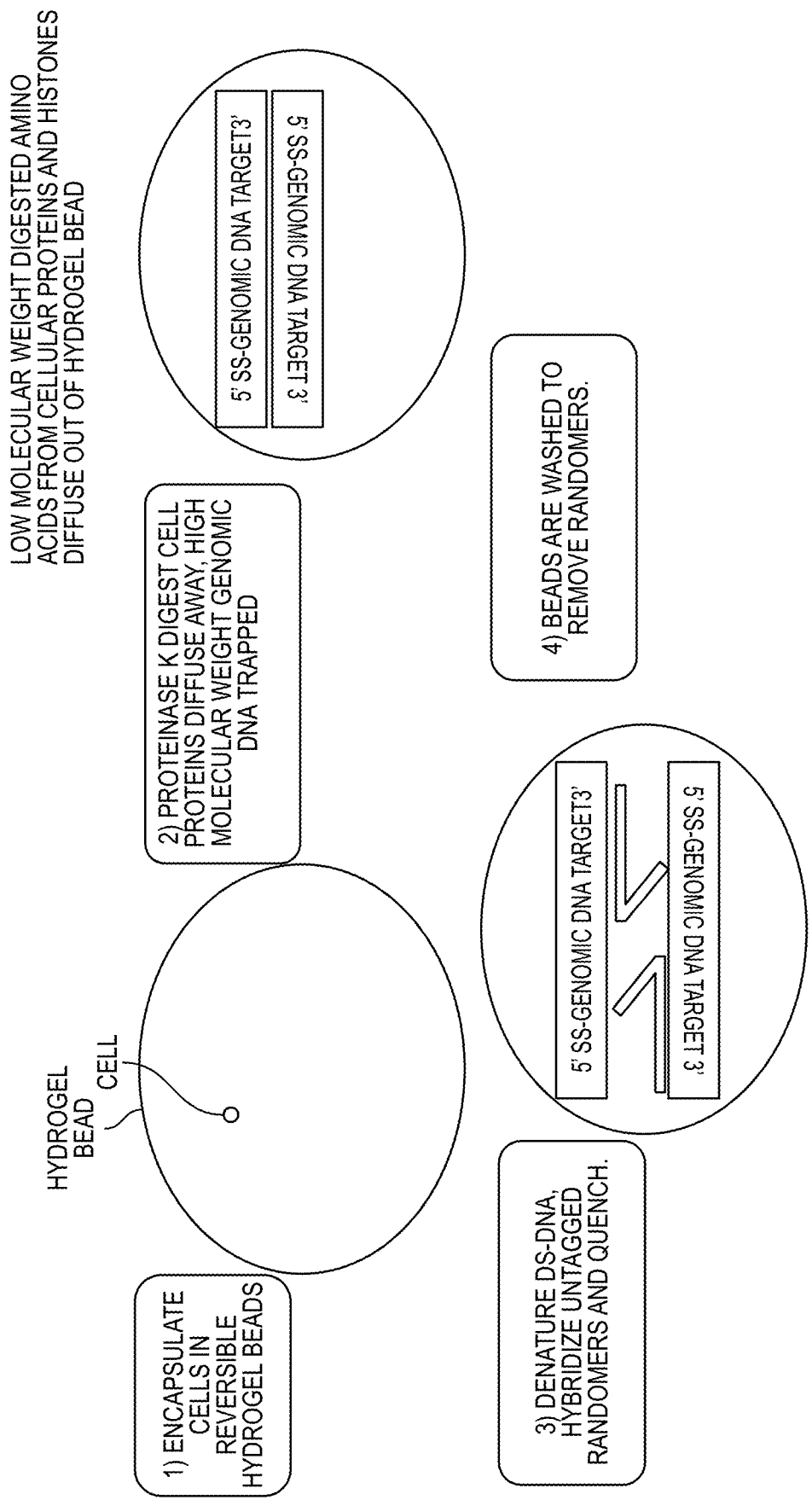
FIG. 6 depicts an initial portion of an MDA method in which a cell is encapsulated in a hydrogel, digested to leave high molecular weight DNA trapped inside, and then the encapsulated cellular DNA is denatured.
Figure 7:
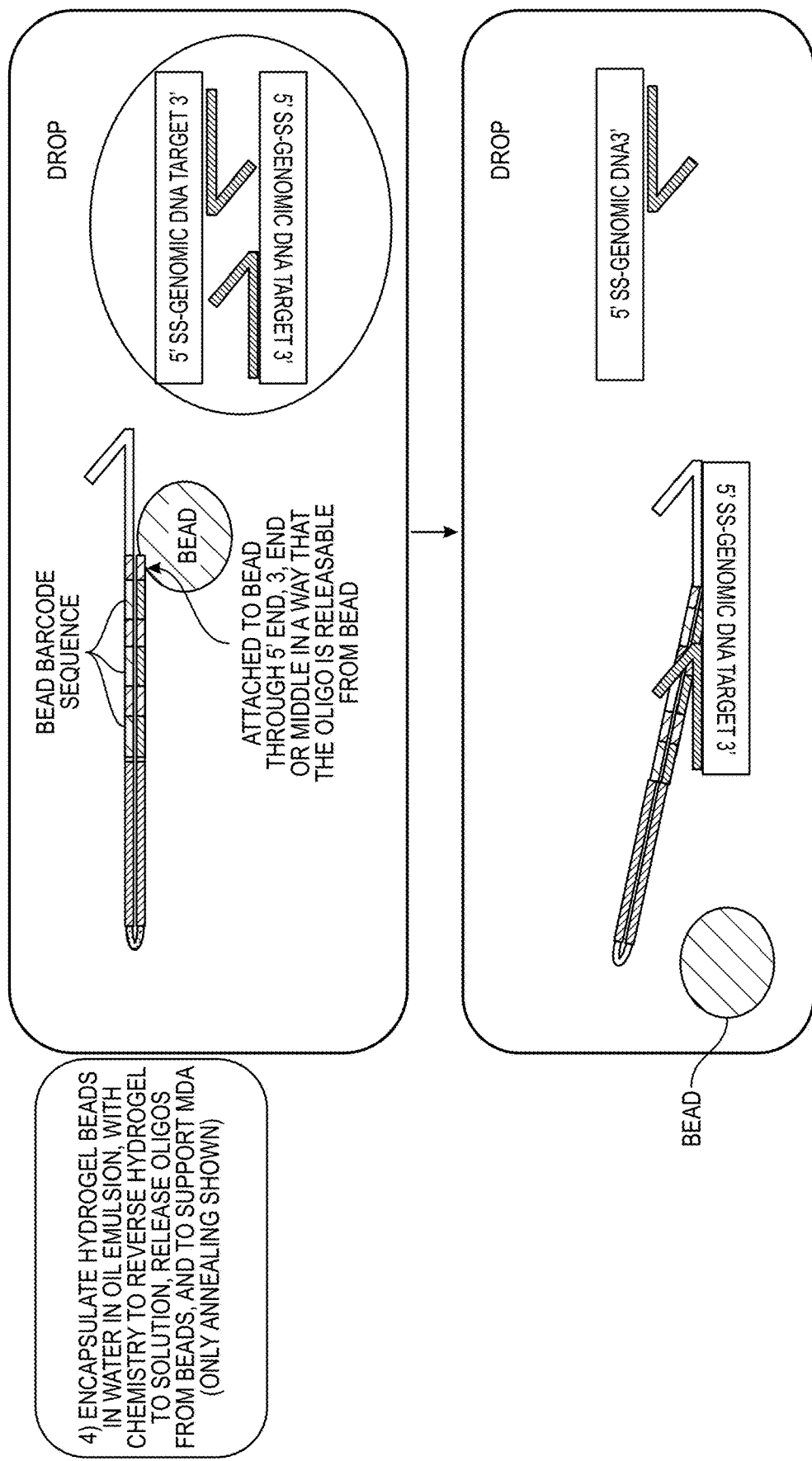
FIG. 7 continues the method of FIG. 6 and shows MDA using the oligonucleotide within a partition (droplet).

In other aspects, methods of performing MDA with the described oligonucleotides from single cells is provided. For example, in some embodiments, a separate cells can be encapsulated within reversible hydrogel beads. Methods of encapsulating cells in hydrogel beads have been described previously, e.g., in Nicodemus, *Tissue Eng Part B Rev.* 2008 June; 14(2): 149-165. Once cells are encapsulated, the cells can be treated with proteinases to remove protein from the cell, leaving higher molecular weight DNA entrapped in the hydrogel. The DNA can be denatured (e.g., with heat or alkaline) and optionally annealed to short denatured random oligonucleotides (e.g., of 5-25 nucleotides in length) as described above to prevent complementary strands of the sample DNA from completely reannealing later. Optionally, the hydrogel beads can be washed to removed excess non-annealed random primers. The encapsulated sample DNA can subsequently be mixed with the oligonucleotides as described herein (i.e., having a 3' randomized sequence, a barcode, optionally an intervening sequence, and linked or separate a complementary sequence as described herein, and optionally linked to a bead) and partitioned together essentially as described in the paragraph above. The oligonucleotide can be released from the bead, if present, in the partition, and MDA can subsequently be performed within the partitions, thereby generating within the partitions barcoded MDA extension products. The partitions can subsequently be combined and the extension products can be characterized (e.g., sequenced), with each partition being represented by a different barcode. Aspects of this method are depicted in FIGS. 6-7.

Following MDA, the extension products can be mixed and sequenced. Any method of nucleotide sequencing can be used as desired so long as at least some of the DNA sample sequence and optionally the barcode sequence is determined. Methods for high throughput sequencing and genotyping are known in the art. For example, such sequencing technologies include, but are not limited to, pyrosequencing, sequencing-by-ligation, single molecule sequencing, sequence-by-synthesis (SBS), massive parallel clonal, massive parallel single molecule SBS, massive parallel single molecule real-time, massive parallel single molecule real-time nanopore technology, etc. Morozova and Marra provide a review of some such technologies in *Genomics*, 92: 255 (2008), herein incorporated by reference in its entirety.

Exemplary DNA sequencing techniques include fluorescence-based sequencing methodologies (See, e.g., Birren et al., Genome Analysis: Analyzing DNA, 1, Cold Spring Harbor, N.Y.; herein incorporated by reference in its entirety). In some embodiments, automated sequencing techniques understood in that art are utilized. In some embodiments, the present technology provides parallel sequencing of partitioned amplicons (PCT Publication No. WO 2006/0841,32, herein incorporated by reference in its entirety). In some embodiments, DNA sequencing is achieved by parallel oligonucleotide extension (See, e.g., U.S. Pat. Nos. 5,750,341; and 6,306,597, both of which are herein incorporated by reference in their entireties). Additional examples of sequencing techniques include the Church polony technology (Mitra et al., 2003, Analytical Biochemistry 320, 55-65; Shendure et al., 2005 Science 309, 1728-1732; and U.S. Pat. Nos. 6,432,360; 6,485,944; 6,511,803; herein incorporated by reference in their entireties), the 454 picotiter pyrosequencing technology (Margulies et al., 2005 Nature 437, 376-380; U.S. Publication No. 2005/0130173; herein incorporated by reference in their entireties), the Solexa single base addition technology (Bennett et al., 2005, Pharmacogenomics, 6, 373-382; U.S. Pat. Nos. 6,787,308; and 6,833,246; herein incorporated by reference in their entireties), the Lynx massively parallel signature sequencing technology (Brenner et al. (2000). Nat. Biotechnol. 18:630-634; U.S. Pat. Nos. 5,695,934; 5,714,330; herein incorporated by reference in their entireties), and the Adessi PCR colony technology (Adessi et al. (2000). Nucleic Acid Res. 28, E87; WO 2000/018957; herein incorporated by reference in its entirety).

Typically, high throughput sequencing methods share the common feature of massively parallel, high-throughput strategies, with the goal of lower costs in comparison to older sequencing methods (See, e.g., Voelkerding et al., Clinical Chem., 55: 641-658, 2009; MacLean et al., Nature Rev. Microbiol., 7:287-296; each herein incorporated by reference in their entirety). Such methods can be broadly divided into those that typically use template amplification and those that do not. Amplification-requiring methods include pyrosequencing commercialized by Roche as the 454 technology platforms (e.g., GS 20 and GS FLX), the Solexa platform commercialized by Illumina, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and platforms commercialized by VisiGen, Oxford Nanopore Technologies Ltd., Life Technologies/Ion Torrent, and Pacific Biosciences, respectively.

In pyrosequencing (Voelkerding et al., Clinical Chem., 55: 641-658, 2009; MacLean et al., Nature Rev. Microbial., 7:287-296; U.S. Pat. Nos. 6,210,891; and 6,258,568; each herein incorporated by reference in its entirety), template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and $10^6$ sequence reads can be achieved, resulting in up to 500 million base pairs (Mb) of sequence.

In the Solexa/Illumina platform (Voelkerding et al., Clinical Chem., 55. 641-658, 2009; MacLean et al., Nature Rev. Microbial., 7:287-296; U.S. Pat. Nos. 6,833,246; 7,115,400; and 6,969,488; each herein incorporated by reference in its entirety), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 50 nucleotides, with overall output exceeding 1 billion nucleotide pairs per analytical run.

Sequencing nucleic acid molecules using SOLiD technology (Voelkerding et al., Clinical Chem., 55: 641-658, 2009; MacLean et al., Nature Rev. Microbial., 7:287-296; U.S. Pat. Nos. 5,912,148; and 6,130,073; each herein incorporated by reference in their entirety) also involves fragmentation of the template, ligation to oligonucleotide adaptors, attachment to beads, and clonal amplification by emulsion PCR. Following this, beads bearing template are immobilized on a derivatized surface of a glass flow-cell, and a primer complementary to the adaptor oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLiD system, interrogation probes have 16 possible combinations of the two bases at the 3' end of each probe, and one of four fluors at the 5' end. Fluor color, and thus identity of each probe, corresponds to specified color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally re-constructed, and template bases are interrogated twice, resulting in increased accuracy. Sequence read length averages 35 nucleotides, and overall output exceeds 4 billion bases per sequencing run.

In certain embodiments, nanopore sequencing is employed (See, e.g., Astier et al., J. Am. Chem. Soc. 2006 Feb. 8; 128(5)1705-10, herein incorporated by reference). The theory behind nanopore sequencing has to do with what occurs when a nanopore is immersed in a conducting fluid and a potential (voltage) is applied across it. Under these conditions a slight electric current due to conduction of ions through the nanopore can be observed, and the amount of current is exceedingly sensitive to the size of the nanopore. As each base of a nucleic acid passes through the nanopore, this causes a change in the magnitude of the current through the nanopore that is distinct for each of the four bases, thereby allowing the sequence of the DNA molecule to be determined.

In certain embodiments, HeliScope by Helicos BioSciences is employed (Voelkerding et al., *Clinical Chem.*, 55. 641-658, 2009; MacLean et al., *Nature Rev. Microbial,* 7:287-296; U.S. Pat. Nos. 7,169,560; 7,282,337; 7,482,120; 7,501,245; 6,818,395; 6,911,345; and 7,501,245; each herein incorporated by reference in their entirety). Template DNA is fragmented and polyadenylated at the 3' end, with the final adenosine bearing a fluorescent label. Denatured polyadenylated template fragments are ligated to poly(dT) oligonucleotides on the surface of a flow cell. Initial physical locations of captured template molecules are recorded by a CCD camera, and then label is cleaved and washed away. Sequencing is achieved by addition of polymerase and serial addition of fluorescently-labeled dNTP reagents. Incorporation events result in fluor signal corresponding to the dNTP, and signal is captured by a CCD camera before each round of dNTP addition. Sequence read length ranges from 25-50 nucleotides, with overall output exceeding 1 billion nucleotide pairs per analytical run.

The Ion Torrent technology is a method of DNA sequencing based on the detection of hydrogen ions that are released during the polymerization of DNA (See, e.g., Science 327 (5970): 1190 (2010); U.S. Pat. Appl. Pub. Nos. 2009/0026082; 2009/0127589; 2010/0301398; 2010/0197507; 2010/0188073; and 2010/0137143, incorporated by reference in their entireties for all purposes). A microwell contains a template DNA strand to be sequenced. Beneath the layer of microwells is a hypersensitive ISFET ion sensor. All layers are contained within a CMOS semiconductor chip, similar to that used in the electronics industry. When a dNTP is incorporated into the growing complementary strand a hydrogen ion is released, which triggers the hypersensitive ion sensor. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics are used. The per base accuracy of the Ion Torrent sequencer is ~99.6% for 50 base reads, with ~100 Mb generated per run. The read-length is 100 base pairs. The accuracy for homopolymer repeats of 5 repeats in length is ~98%. The benefits of ion semiconductor sequencing are rapid sequencing speed and low upfront and operating costs.

Another exemplary nucleic acid sequencing approach that may be adapted for use with the present invention was developed by Stratos Genomics, Inc. and involves the use of Xpandomers. This sequencing process typically includes providing a daughter strand produced by a template-directed synthesis. The daughter strand generally includes a plurality of subunits coupled in a sequence corresponding to a contiguous nucleotide sequence of all or a portion of a target nucleic acid in which the individual subunits comprise a tether, at least one probe or nucleobase residue, and at least one selectively cleavable bond. The selectively cleavable bond(s) is/are cleaved to yield an Xpandomer of a length longer than the plurality of the subunits of the daughter strand. The Xpandomer typically includes the tethers and reporter elements for parsing genetic information in a sequence corresponding to the contiguous nucleotide sequence of all or a portion of the target nucleic acid. Reporter elements of the Xpandomer are then detected. Additional details relating to Xpandomer-based approaches are described in, for example, U.S. Pat. Pub No. 2009/0035777, which is incorporated herein in its entirety.

Other single molecule sequencing methods include real-time sequencing by synthesis using a VisiGen platform (Voelkerding et al., Clinical Chem., 55: 641-58, 2009; U.S. Pat. No. 7,329,492; and U.S. patent application Ser. Nos. 11/671,956; and 11/781,166; each herein incorporated by reference in their entirety) in which immobilized, primed DNA template is subjected to strand extension using a fluorescently-modified polymerase and florescent acceptor molecules, resulting in detectible fluorescence resonance energy transfer (FRET) upon nucleotide addition.

Another real-time single molecule sequencing system developed by Pacific Biosciences (Voelkerding et al., Clinical Chem., 55. 641-658, 2009; MacLean et al., Nature Rev. Microbiol., 7:287-296; U.S. Pat. Nos. 7,170,050; 7,302,146; 7,313,308; and 7,476,503; all of which are herein incorporated by reference) utilizes reaction wells 50-100 nm in diameter and encompassing a reaction volume of approximately 20 zeptoliters ($10^{-21}$ L). Sequencing reactions are performed using immobilized template, modified phi29 DNA polymerase, and high local concentrations of fluorescently labeled dNTPs. High local concentrations and continuous reaction conditions allow incorporation events to be captured in real time by fluor signal detection using laser excitation, an optical waveguide, and a CCD camera.

In certain embodiments, the single molecule real time (SMRT) DNA sequencing methods using zero-mode waveguides (ZMWs) developed by Pacific Biosciences, or similar methods, are employed. With this technology, DNA sequencing is performed on SMRT chips, each containing thousands of zero-mode waveguides (ZMWs). A ZMW is a hole, tens of nanometers in diameter, fabricated in a 100 nm metal film deposited on a silicon dioxide substrate. Each ZMW becomes a nanophotonic visualization chamber providing a detection volume of just 20 zeptoliters ($10^{-21}$ L). At this volume, the activity of a single molecule can be detected amongst a background of thousands of labeled nucleotides. The ZMW provides a window for watching DNA polymerase as it performs sequencing by synthesis. Within each chamber, a single DNA polymerase molecule is attached to the bottom surface such that it permanently resides within the detection volume. Phospholinked nucleotides, each type labeled with a different colored fluorophore, are then introduced into the reaction solution at high concentrations which promote enzyme speed, accuracy, and processivity. Due to the small size of the ZMW, even at these high concentrations, the detection volume is occupied by nucleotides only a small fraction of the time. In addition, visits to the detection volume are fast, lasting only a few microseconds, due to the very small distance that diffusion has to carry the nucleotides. The result is a very low background.

Processes and systems for such real time sequencing that may be adapted for use with the invention are described in, for example, U.S. Pat. Nos. 7,405,281; 7,315,019; 7,313,308; 7,302,146; and 7,170,050; and U.S. Pat. Pub. Nos. 2008/0212960; 2008/0206764; 2008/0199932; 2008/0199874; 2008/0176769; 2008/0176316; 2008/0176241; 2008/0165346; 2008/0160531; 2008/0157005; 2008/0153100; 2008/0153095; 2008/0152281; 2008/0152280; 2008/0145278; 2008/0128627; 2008/0108082; 2008/0095488; 2008/0080059; 2008/0050747; 2008/0032301; 2008/0030628; 2008/0009007; 2007/0238679; 2007/0231804; 2007/0206187; 2007/0196846; 2007/0188750; 2007/0161017; 2007/0141598; 2007/0134128; 2007/0128133; 2007/0077564; 2007/0072196; and 2007/0036511; and Korlach et al. (2008) "Selective aluminum passivation for targeted immobilization of single DNA polymerase molecules in zero-mode waveguide nanostructures" PNAS 105(4): 1176-81, all of which are herein incorporated by reference in their entireties.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A plurality of oligonucleotides of different sequence, the oligonucleotides of different sequence covalently linked to separate solid support beads, the oligonucleotides comprising a 3' random sequence of at least four contiguous nucleotides, a barcode sequence, and one or more nucleotide sequences, the oligonucleotides annealed to a complementary nucleic acid that is complementary to some or all of the nucleotide sequence, wherein the complementary nucleic acid is not complementary to the barcode sequence or the 3' random sequence, leaving the 3' random sequence to be single-stranded, wherein the nucleotide sequence is:

(i) 5' to the barcode sequence, or (ii) a sequence that divides the barcode into two or more barcode portions, wherein the barcode portions are separated by the nucleotide sequence.

2. The plurality of oligonucleotides of claim 1, wherein the plurality comprises at least 25 different oligonucleotides having different random sequences.

3. The plurality of oligonucleotides of claim 1, wherein the oligonucleotides further comprise a 5' tag sequence.

4. The plurality of oligonucleotides of claim 3, wherein the 5' tag sequence is covalently linked to a solid support bead.

5. The plurality of oligonucleotides of claim 1, wherein the nucleotide intervening sequence is 5' to the barcode sequence.

6. The plurality of oligonucleotides of claim 1, wherein the nucleotide sequence is the sequence that divides the barcode into two or more barcode portions, wherein the barcode portions are separated by the nucleotide sequence.

7. The plurality of oligonucleotides of claim 1, wherein the complementary nucleic acid is not covalently linked to the oligonucleotides.

8. The plurality of oligonucleotides of claim 1, wherein the solid support beads are in partitions and the partitions on average comprise 1-3 solid support beads.

9. The plurality of oligonucleotides of claim 8, wherein the partitions are droplets within an emulsion.

10. The plurality of oligonucleotides of claim 1, wherein the solid support beads are in a bulk reaction mixture.

11. The plurality of oligonucleotides of claim 1, wherein the complementary nucleic acid comprises one or more nucleotide that is incompatible with the strand-displacing polymerase.

12. The plurality of oligonucleotides of claim 1, wherein the complementary nucleic acid comprises one or more nucleotide that is incompatible with a phi29 polymerase.

13. The plurality of oligonucleotides of claim 1, wherein the solid support beads are in droplets further comprising sample DNA encapsulated in a hydrogel bead.

14. The plurality of oligonucleotides of claim 13, wherein the sample DNA in the hydrogel consists of DNA from one or more cell.

* * * * *

SEQUENCE LISTING

```
Sequence total quantity: 3
SEQ ID NO: 1            moltype = DNA   length = 33
FEATURE                 Location/Qualifiers
misc_feature            1..33
                        note = Synthetic construct
source                  1..33
                        mol_type = other DNA
                        organism = synthetic construct
SEQUENCE: 1
acactctttc cctacacgac gctcttccga tct                                33

SEQ ID NO: 2            moltype = DNA   length = 25
FEATURE                 Location/Qualifiers
misc_feature            1..25
                        note = Synthetic construct
source                  1..25
                        mol_type = other DNA
```

```
                        organism = synthetic construct
SEQUENCE: 2
aatgatacgg cgaccaccga gatct                                         25

SEQ ID NO: 3            moltype = DNA  length = 24
FEATURE                 Location/Qualifiers
misc_feature            1..24
                        note = Synthetic construct
source                  1..24
                        mol_type = other DNA
                        organism = synthetic construct
SEQUENCE: 3
caagcagaag acggcatacg agat                                          24
```